United States Patent
Shimizu et al.

(10) Patent No.: US 8,029,436 B2
(45) Date of Patent: Oct. 4, 2011

(54) POWER SUPPLY APPARATUS FOR A BODY INSERTABLE APPARATUS

(75) Inventors: Hatsuo Shimizu, Tokyo (JP); Takemitsu Honda, Tokyo (JP); Tetsuo Minai, Tokyo (JP); Kazutaka Nakatsuchi, Tokyo (JP)

(73) Assignee: Olympus Corporation (JP)

( * ) Notice: Subject to any disclaimer, the term of this patent is extended or adjusted under 35 U.S.C. 154(b) by 1288 days.

(21) Appl. No.: 11/536,150

(22) Filed: Sep. 28, 2006

(65) Prior Publication Data

US 2007/0032697 A1 Feb. 8, 2007

Related U.S. Application Data

(63) Continuation of application No. PCT/JP2005/005421, filed on Mar. 24, 2005.

(30) Foreign Application Priority Data

Mar. 29, 2004 (JP) ................................ 2004-095880

(51) Int. Cl.
*A61B 1/00* (2006.01)
(52) U.S. Cl. ...................................... 600/101; 600/118
(58) Field of Classification Search .................. 600/101, 600/109, 302, 424, 118
See application file for complete search history.

(56) References Cited

U.S. PATENT DOCUMENTS

| | | | |
|---|---|---|---|
| 4,278,077 A | 7/1981 | Mizumoto | 128/4 |
| 4,685,462 A * | 8/1987 | Olsen | 607/98 |
| 5,343,862 A * | 9/1994 | Jones | 600/422 |
| 6,200,259 B1 * | 3/2001 | March | 600/9 |
| 6,632,216 B2 * | 10/2003 | Houzego et al. | 604/890.1 |
| 7,354,398 B2 * | 4/2008 | Kanazawa | 600/109 |
| 7,604,591 B2 * | 10/2009 | Uchiyama et al. | 600/130 |
| 7,618,366 B2 * | 11/2009 | Glukhovsky et al. | 600/101 |
| 2002/0151788 A1 * | 10/2002 | Menon | 600/421 |
| 2002/0154518 A1 * | 10/2002 | Elferich et al. | 363/15 |
| 2002/0165592 A1 * | 11/2002 | Glukhovsky et al. | 607/62 |
| 2003/0085994 A1 | 5/2003 | Fujita et al. | 348/77 |
| 2003/0158585 A1 * | 8/2003 | Burnett | 607/2 |
| 2004/0181127 A1 * | 9/2004 | Matsumoto et al. | 600/101 |
| 2006/0084380 A1 * | 4/2006 | Hoyt et al. | 455/41.1 |
| 2007/0185382 A1 * | 8/2007 | Shimizu et al. | 600/118 |
| 2007/0270630 A1 * | 11/2007 | Houzego et al. | 600/12 |

FOREIGN PATENT DOCUMENTS

| | | |
|---|---|---|
| JP | 62-284498 | 12/1987 |
| JP | 01-129540 | 5/1989 |
| JP | 06-078477 A | 3/1994 |

(Continued)

OTHER PUBLICATIONS

International Search Report dated Jun. 24, 2005.

(Continued)

*Primary Examiner* — John P Leubecker
(74) *Attorney, Agent, or Firm* — Ostrolenk Faber LLP (57) ABSTRACT

A power supply apparatus supplies power to a body-insertable apparatus from outside a subject. The body-insertable apparatus is introduced into the subject and obtains intra-subject information. The power supply apparatus includes a first electric cable which is wound around a circumferential surface of a garment and forms a coil, the garment covering the subject, the coil having a non-directionality at a time of power supply; and a power supply unit which supplies power to the body-insertable apparatus in a contactless manner through the coil.

1 Claim, 12 Drawing Sheets

FOREIGN PATENT DOCUMENTS

| | | |
|---|---|---|
| JP | 10-242736 | 9/1998 |
| JP | 2001-231186 A | 8/2001 |
| JP | 2001-231187 | 8/2001 |
| JP | 2004-073725 | 3/2004 |
| JP | 2004-159456 | 6/2004 |
| JP | 2005-052365 | 3/2005 |
| JP | 2005-066095 | 3/2005 |
| JP | 2005-124314 | 5/2005 |
| WO | WO 01/95432 A1 | 12/2001 |
| WO | WO 02/080753 | 10/2002 |

OTHER PUBLICATIONS

Office Action issued by Japanese Patent Office on Sep. 4, 2007 in connection with corresponding application No. 2004-095880.
Partial English translation of Japanese Office Action submitted in lieu of a Statement of Relevancy of the present invention to the teachings of the cited prior art, Sep. 4, 2007.

* cited by examiner

POWER SUPPLY APPARATUS FOR A BODY INSERTABLE APPARATUS

CROSS-REFERENCE TO RELATED APPLICATIONS

This application is a continuation of PCT international application Ser. No. PCT/JP2005/005421 filed Mar. 24, 2005 which designates the United States, incorporated herein by reference, and which claims the benefit of priority from Japanese Patent Application No. 2004-095880 filed Mar. 29, 2004, incorporated herein by reference.

BACKGROUND OF THE INVENTION

1. Field of the Invention

The present invention relates to a power supply apparatus which supplies power to a body-insertable apparatus in a subject from outside the subject. The body-insertable apparatus is exemplified by a swallowable capsule endoscope.

2. Description of the Related Art

In recent years, a capsule endoscope equipped with an imaging function and a radio function has appeared in the endoscope field. The capsule endoscope is moved in internal organs such as a stomach and a small intestine (or in body cavities) with peristaltic motion thereof to sequentially perform imaging in the body cavities using the imaging function in an observation period during which the capsule endoscope is swallowed into a subject as a tested body for observation (examination) and is naturally discharged from the living body as the subject.

Image data imaged in the body cavities by the capsule endoscope in the observation period of movement in these internal organs is sequentially transmitted to an external device provided outside the subject by the radio function such as radio communication and is then stored in a memory provided in the external device. The subject carries the external device having the radio function and the memory function. The subject can be freely moved in the observation period during which the capsule endoscope is swallowed and discharged. After observation, a doctor or a nurse can display the images in the body cavities on a display device such as a display based on the image data stored in the memory of the external device to perform diagnosis.

JP-A No. 2001-231186 (KOKAI) (page 3, FIG. 1) shows one conventional system for supplying power to the capsule endoscope of the above-described type. When a radio capsule (corresponding to the capsule endoscope) is placed inside the living subject, the system transmits the power from outside the subject to an inside of the capsule endoscope. The system includes an external device having a power-transmitting antenna and the capsule endoscope having a power-receiving antenna arranged therein. The external device supplies power to the capsule endoscope through the power-transmitting antenna and the power-receiving antenna, whereby the capsule endoscope can perform an observation operation in the subject for an extended period of time.

SUMMARY OF THE INVENTION

A power supply apparatus according to one aspect of the present invention supplies power to a body-insertable apparatus from outside a subject, and the body-insertable apparatus is introduced into the subject and obtains intra-subject information. The power supply apparatus according to one aspect of the present invention includes a first electric cable which is wound around a circumferential surface of a garment and forms a coil, the garment covering the subject, the coil having a non-directionality at a time of power supply; and a power supply unit which supplies power to the body-insertable apparatus in a contactless manner through the coil.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a power supply apparatus according to the present invention will be described in detail with reference to FIGS. 1 to 12. The power supply apparatus of the present invention supplies power to an intra-subject information acquiring device. It should be noted that the present invention is not limited to the embodiments as described below, and various modifications and alternations can be made to the embodiments without departing from a scope of the present invention.

Figure 1:
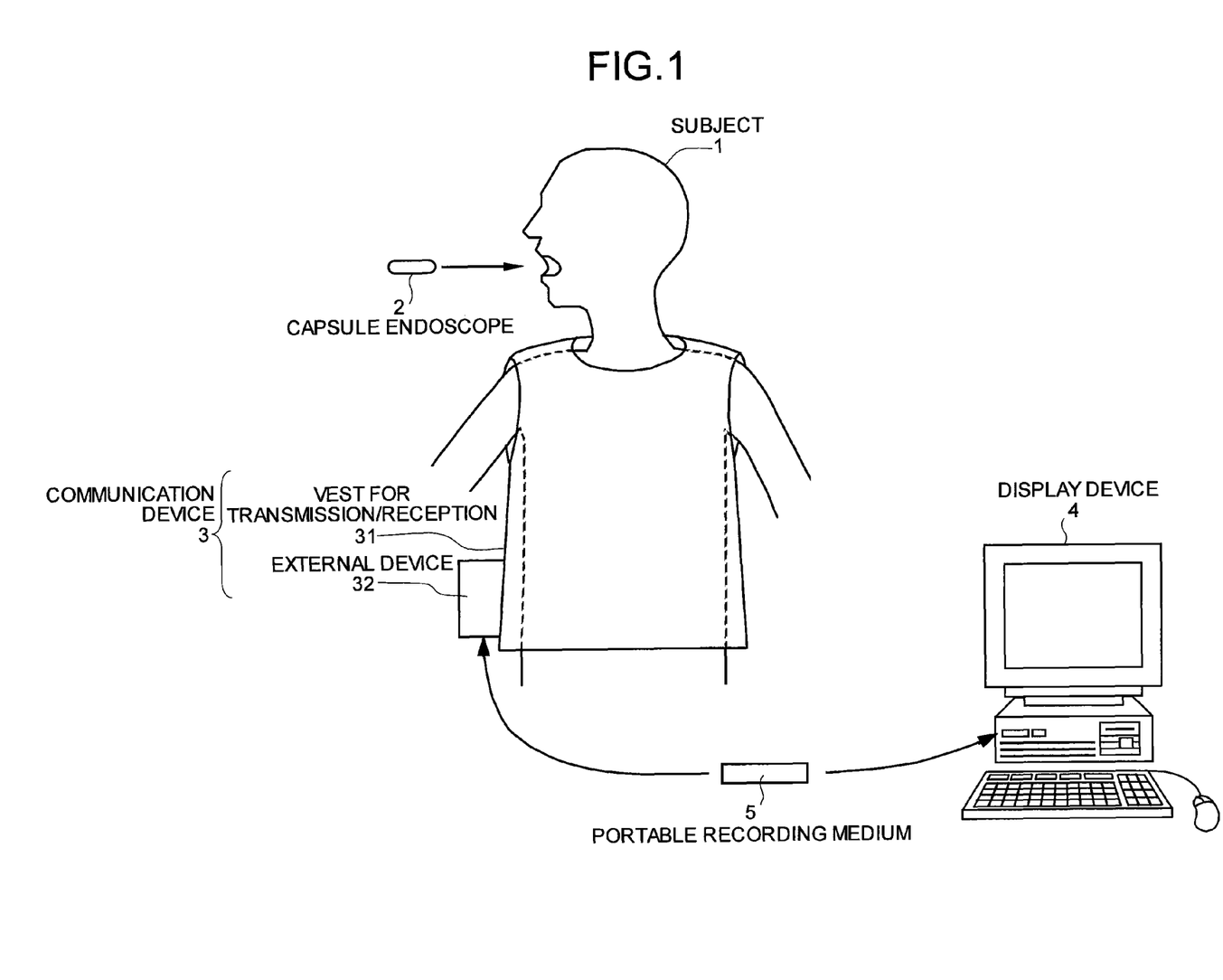
FIG. 1 shows an overall configuration of an intra-subject information obtaining system according to the present invention.

As shown in FIG. 1, the intra-subject information obtaining system includes a swallowable capsule endoscope 2 and a communication device 3, a display device 4, and a portable recording medium 5. A subject 1 swallows the capsule endoscope 2. The capsule endoscope 2 is introduced into a body cavity of the subject 1 and functions as the intra-subject information acquiring device. The communication device 3 is arranged outside the subject 1 and serves as an external device to the subject. The communication device 3 transmits various types of information to/from the capsule endoscope 2 by radio communication. The communication device 3 receives data sent from the capsule endoscope 2, and the display device 4 presents an image based on the received data. The portable recording medium 5 serves to deliver data between the communication device 3 and the display device 4.

In FIGS. 2 to 12, the same elements as those shown in FIG. 1 will be denoted by the same reference characters for convenience of description. As shown in the block diagram of FIG. 2, the capsule endoscope 2 includes a light emitting diode (LED) 20, an LED driving circuit 21, a charge coupled device (CCD) 22, a CCD driving circuit 23, an RF transmitting unit 24, and a transmitting antenna unit 25. The LED 20 serves as an illuminating unit that illuminates an examined region inside the body cavity of the subject 1. The LED driving circuit 21 controls a driven state of the LED 20. Light emitted from the LED 20 is reflected by the examined region inside the body cavity and forms an image. The CCD 22 serves as a sensor unit (imaging unit) that picks up the thus formed image (intra-subject information). The CCD driving circuit 23 controls a driven state of the CCD 22. The picked-up image, as an image signal, is modulated by the RF transmitting unit 24 that serves as a radio transmission unit and outputted as an RF signal. The RF signal is then sent by the transmitting antenna unit 25 by radio communication.

Figure 2:
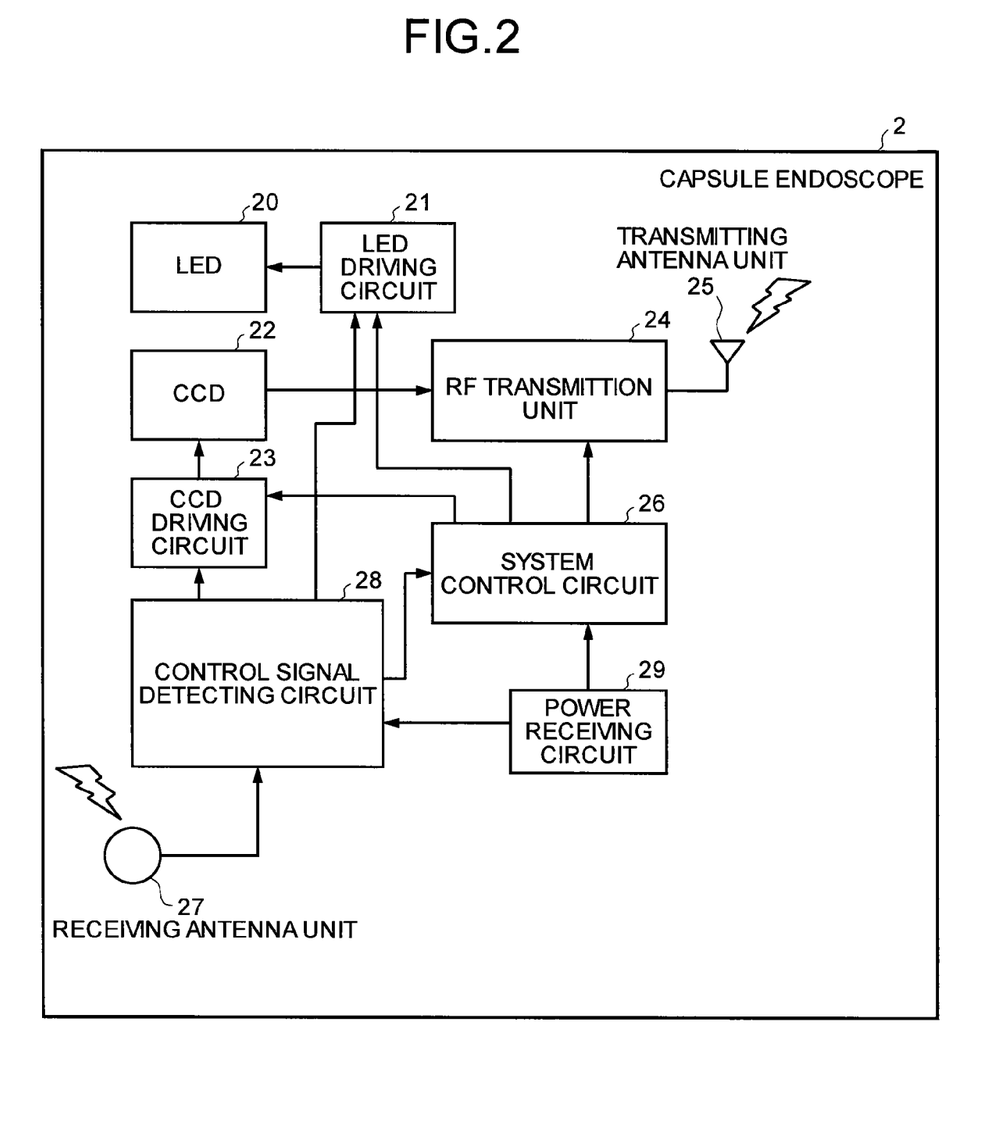
FIG. 2 is a block diagram showing an inner configuration of a capsule endoscope shown in FIG. 1.

The capsule endoscope 2 further includes a system control circuit 26. The system control circuit 26 controls the operations of the LED driving circuit 21, the CCD driving circuit 23, and the RF transmitting unit 24, so that CCD 22 can obtain image data of the examined region illuminated by the LED 20 while the capsule endoscope 2 is inside the subject 1. The obtained image data is converted into the RF signal by the RF transmitting unit 24. The RF signal is then transmitted to the outside of the subject 1 through the transmitting antenna unit 25.

Further, the capsule endoscope 2 includes a receiving antenna unit 27, a control signal detecting circuit 28, and a power receiving circuit 29. The receiving antenna unit 27 serves as a radio receiving unit and is able to receive a radio signal transmitted from the communication device 3. The control signal detecting circuit 28 detects a signal which has a predetermined input level (e.g., reception strength level) as a control signal from among the signals received by the receiving antenna unit 27. The power receiving circuit 29 supplies power to the system control circuit 26 and the control signal detecting circuit 28.

The control signal detecting circuit 28 detects a signal having a higher level than the predetermined input level (as an activation signal) from among the received signals. The control signal detecting circuit 28 supplies the activation signal to the system control circuit 26. Further, the control signal detecting circuit 28 detects a content of the control signal and outputs the control signal to the LED driving circuit 21, the CCD driving circuit 23, and the system control circuit 26, as necessary. The system control circuit 26 has a function of distributing driving power supplied from the power receiving circuit 29 to other elements, i.e., to function executing units.

The system control circuit 26 includes a switch element, latch circuit, or the like connected between the power receiving circuit 29 and each of the other elements. The switch element and the latch circuit have a switching function. When the magnetic field is externally applied, the latch circuit turns the switch element on, and maintains the on-state of the switch element to let the driving power from the power receiving circuit 29 be supplied to each component in the capsule endoscope 2. In the first embodiment, the "function executing unit" is a generic term referring to elements that execute a predetermined function in the capsule endoscope 2, such as the imaging unit having an imaging function, the illuminating unit having an illumination function, and the radio transmission unit having (a part of) radio communication function. The imaging unit and the illuminating unit are also referred to as a first function executing unit; and the radio transmission unit is referred to as a second function executing unit. Specifically, elements other than the system control circuit 26, the receiving antenna unit 27, and the control signal detecting circuit 28 are the function executing units that execute a predetermined function. In the following, the function executing units will be collectively referred to as intra-capsule function executing circuit if necessary.

Figure 3:
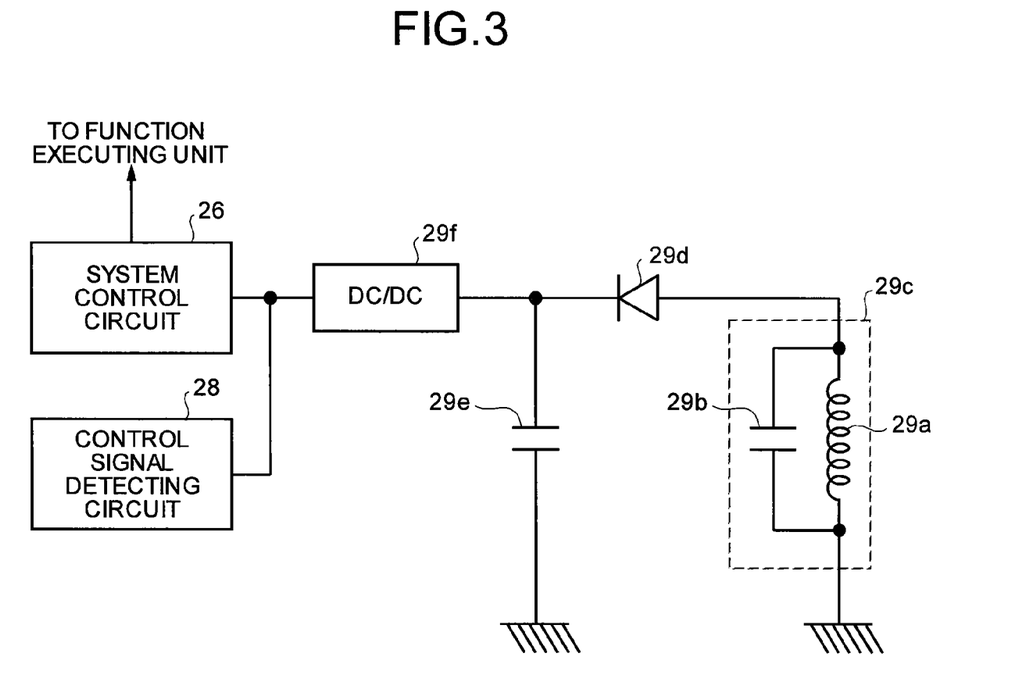
FIG. 3 is a circuit diagram showing a circuit structure of a power receiving circuit shown in FIG. 2.

As shown in FIG. 3, the power receiving circuit 29 includes a power receiving resonance circuit 29c, a rectifying diode 29d, a capacitor 29e, and a DC/DC converter 29f. The power receiving resonance circuit 29c has a power receiving coil 29a and a capacitor 29b that are formed to have a resonance frequency matched with the frequency of a transmitted power signal. The rectifying diode 29d converts an alternate current signal into a direct current signal. The capacitor 29e accumulates power rectified by the rectifying diode 29d. The DC/DC converter 29f serves as a booster that boosts the power supplied from the capacitor 29e. In brief, in the power receiving circuit 29, the power signal is received at the power receiving resonance circuit 29c, rectified by the rectifying diode 29d, and accumulated in the capacitor 29e sequentially. The accumulated power is boosted by the DC/DC converter 29f so that the accumulated power can be employed as the driving power for each of the function executing units. After the boosting, the power is supplied to the system control circuit 26 and the control signal detecting circuit 28 in the capsule endoscope 2. Thereafter, the power is distributed to each of the function executing units that operate thereby.

Figure 4:
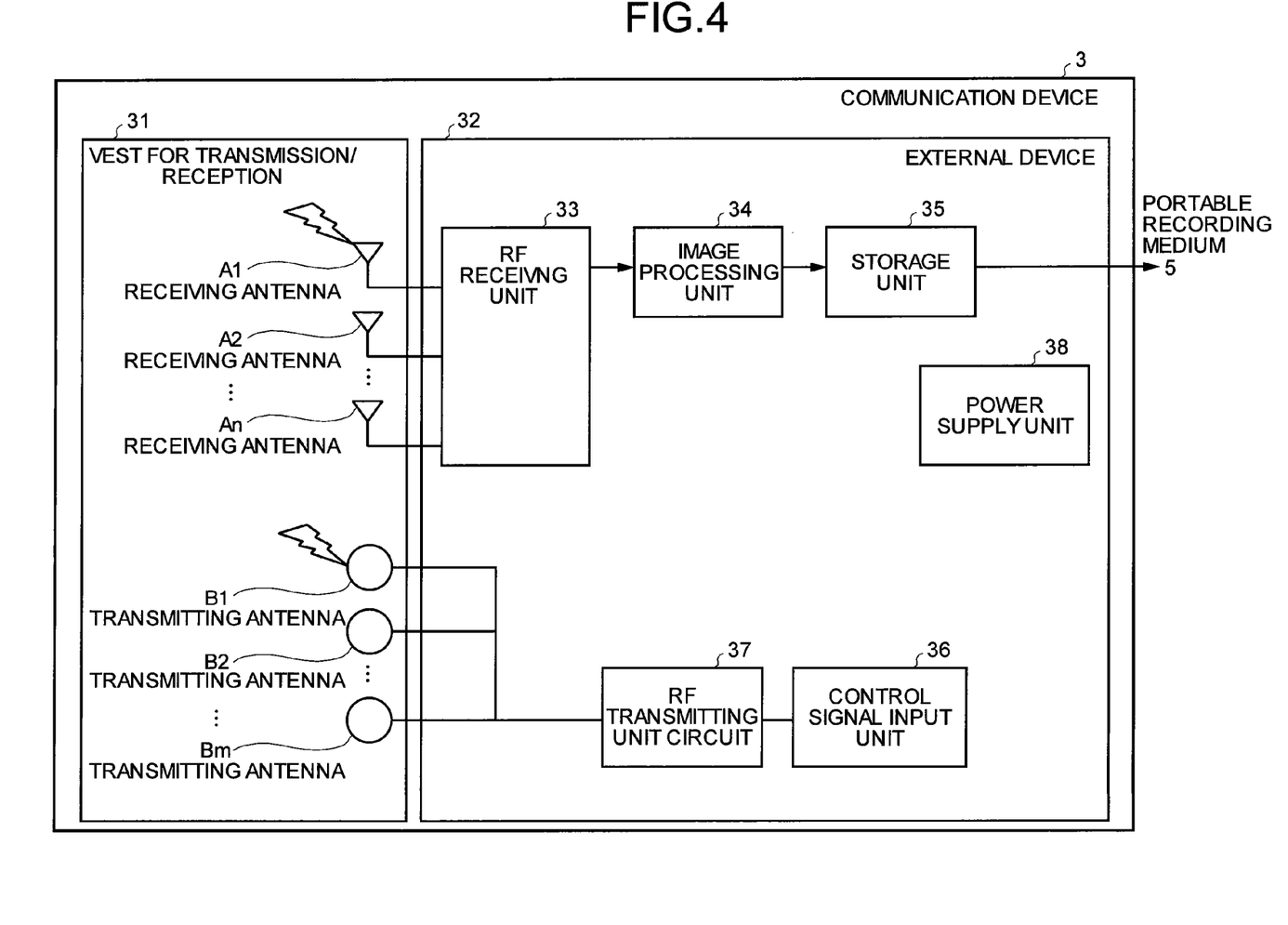
FIG. 4 is a block diagram showing an inner structure of a communication device shown in FIG. 1.

The communication device 3 has functions of both a transmitter (ratio transmission unit) and a receiver (radio receiving unit). Specifically, the communication device 3 transmits the activation signal to the capsule endoscope 2 on one hand, and receives the image data of inside the body cavity sent from the capsule endoscope 2 by radio communication on the other hand. The inner structure of the communication device 3 will be described with reference to FIG. 4. As shown in FIG. 4, the communication device 3 includes a garment 31 (e.g., vest) for transmission/reception and an external device 32. The vest 31 includes plural receiving antennae A1 to An and plural transmitting antennae B1 to Bm. During operation, the subject 1 wears the vest 31. The external device 32 performs various processing such as signal processing on radio signals which are received or to be sent. In the above, characters "n" and "m" indicate the number of the antennae, which can be set to any number as necessary.

The external device 32 performs signal processing on the radio signal transmitted from the capsule endoscope 2, and includes an RF receiving unit 33, an image processing unit 34, and a storage unit 35. The RF receiving unit 33 performs predetermined signal processing, such as demodulation on the radio signal received by the receiving antennae A1 to An, and extracts the image data obtained by the capsule endoscope 2 from the radio signal. The image processing unit 34 performs necessary image processing on the extracted image data. The processed image data is stored in the storage unit 35. In the first embodiment, the image data is stored in the portable recording medium 5 through the storage unit 35.

Further, the external device 32 includes a control signal input unit 36 and an RF transmission unit circuit 37. The control signal input unit 36 generates the control signal (activation signal) to control the driven state of the capsule endoscope 2. The RF transmission unit circuit 37 converts the generated control signal into a radio frequency for output. The signal after the conversion by the RF transmission unit circuit 37 is supplied to the transmitting antennae B1 to Bm to be transmitted to the capsule endoscope 2. Still further, the external device 32 includes a power supply unit 38 which is provided with a predetermined condenser, an AC power supply adapter, or the like. Each of the elements in the external device 32 consumes the power supplied from the power supply unit 38 as driving energy. The power supply unit 38 also supplies power to a driver circuit of a coil-like electric cable (hereinbelow simply referred to as "coil") arranged in the garment 31 such as a vest, which will be described later.

The display device 4 serves to show an intra-body-cavity image that is obtained by the capsule endoscope 2. The display device 4 is configured as a workstation that displays an image based on data read from the portable recording medium 5. Specifically, the display device 4 may include a CRT display or a liquid crystal display to directly present the image thereon, or may be configured as a printer or the like to output the image onto other medium.

The portable recording medium 5 can be connected to both the external device 32 and the display device 4. When the portable recording medium 5 is inserted into and connected to one of the external device 32 and the display device 4, the information stored therein can be read out or the information can be recorded into the portable recording medium 5. In the first embodiment, while the capsule endoscope 2 is moving inside the body cavity of the subject 1, the portable recording medium 5 is placed into the external device 32 and records data sent from the capsule endoscope 2. After the capsule endoscope 2 is discharged from the subject 1, in other words, when the imaging of inside the subject 1 is finished, the portable recording medium 5 is taken out from the external device 32 and inserted into the display device 4. Then the display device 4 reads out the data recorded in the portable recording medium 5. The portable recording medium 5 is configured of, for example, a Compact Flash (registered trademark) memory. When the portable recording medium 5 is employed, data transfer between the external device 32 and the display device 4 can be indirectly performed. Thus, dissimilar to systems which directly connect the external device 32 and the display 4 by a cable or the like, the system of the embodiment allows the subject 1 to move freely while the capsule endoscope 2 picks up the images of inside the body cavity.

Figure 5:
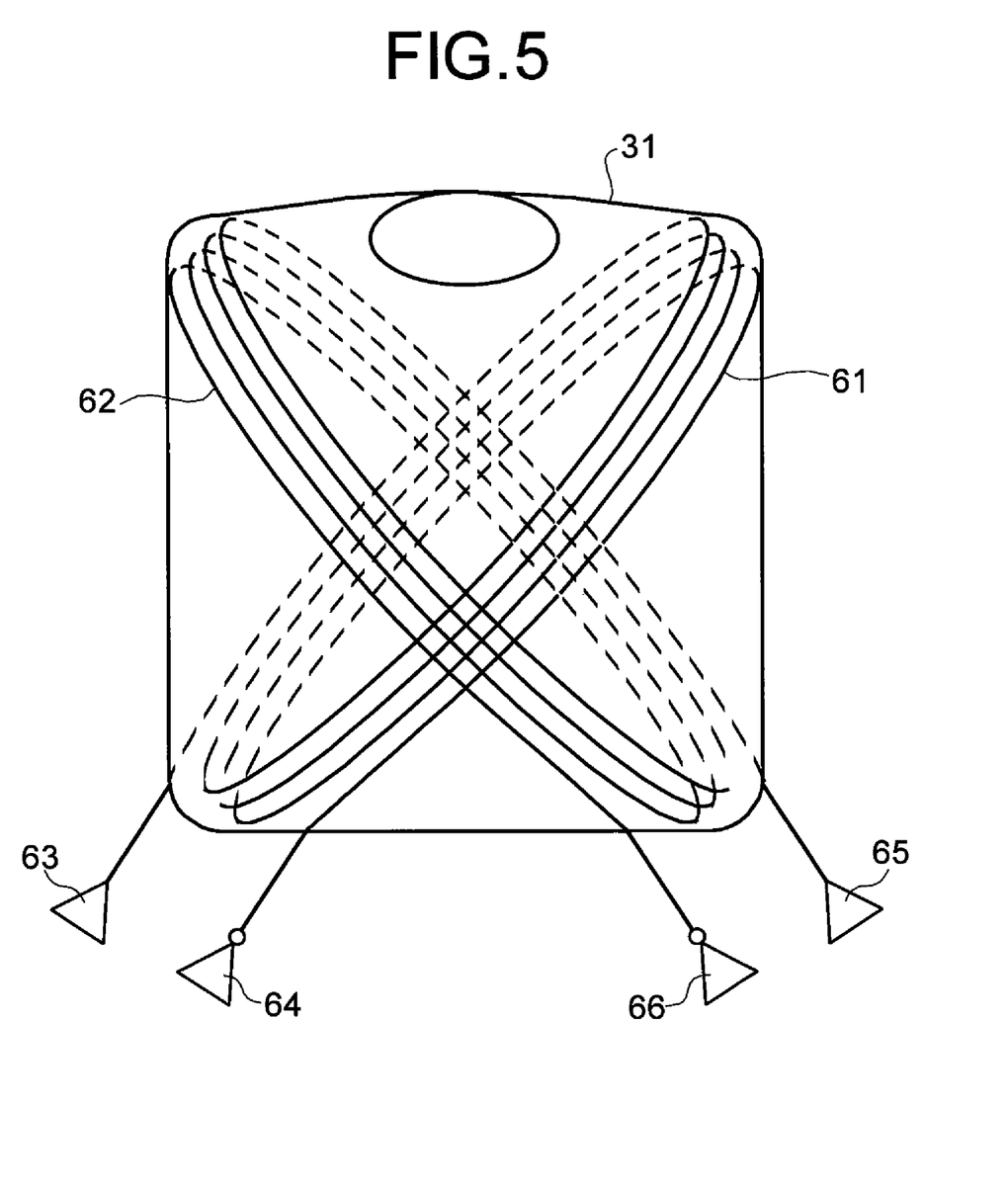
FIG. 5 is a frontal view showing a first embodiment of a vest shown in FIG. 1.

The garment 31 of the first embodiment will be described with reference to the frontal view of FIG. 5. In FIG. 5 two strands of electric cable form two coils, i.e., coils 61 and 62, and are arranged in the garment 31. Each of the coils 61 and 62 runs obliquely along the inner circumferential surface of the pullover garment (vest, for example) 31 and is wound. The coils 61 and 62 are symmetrically arranged. When the subject wears the vest 31, the coil 61 runs from the left shoulder to the right waist and forms spiral loops of a predetermined pitch while the coil 62 runs from the right shoulder to the left waist and forms spiral loops of a predetermined pitch. The coils 61 and 62 intersect with each other on a center line of the subject body.

The coils 61 and 62 are connected to driver circuits 63 to 66, that are further connected to the power supply unit 38 of the above-described external device 32. The power supply unit 38 supplies power through the driver circuit 63 to 66 to the coils 61 and 62, which generates an alternate current magnetic field of a predetermined strength on each of the coils 61 and 62. The vest 31 also includes the plural receiving antennae A1 to An and the plural transmitting antennae B1 to Bm not shown.

Figure 6:
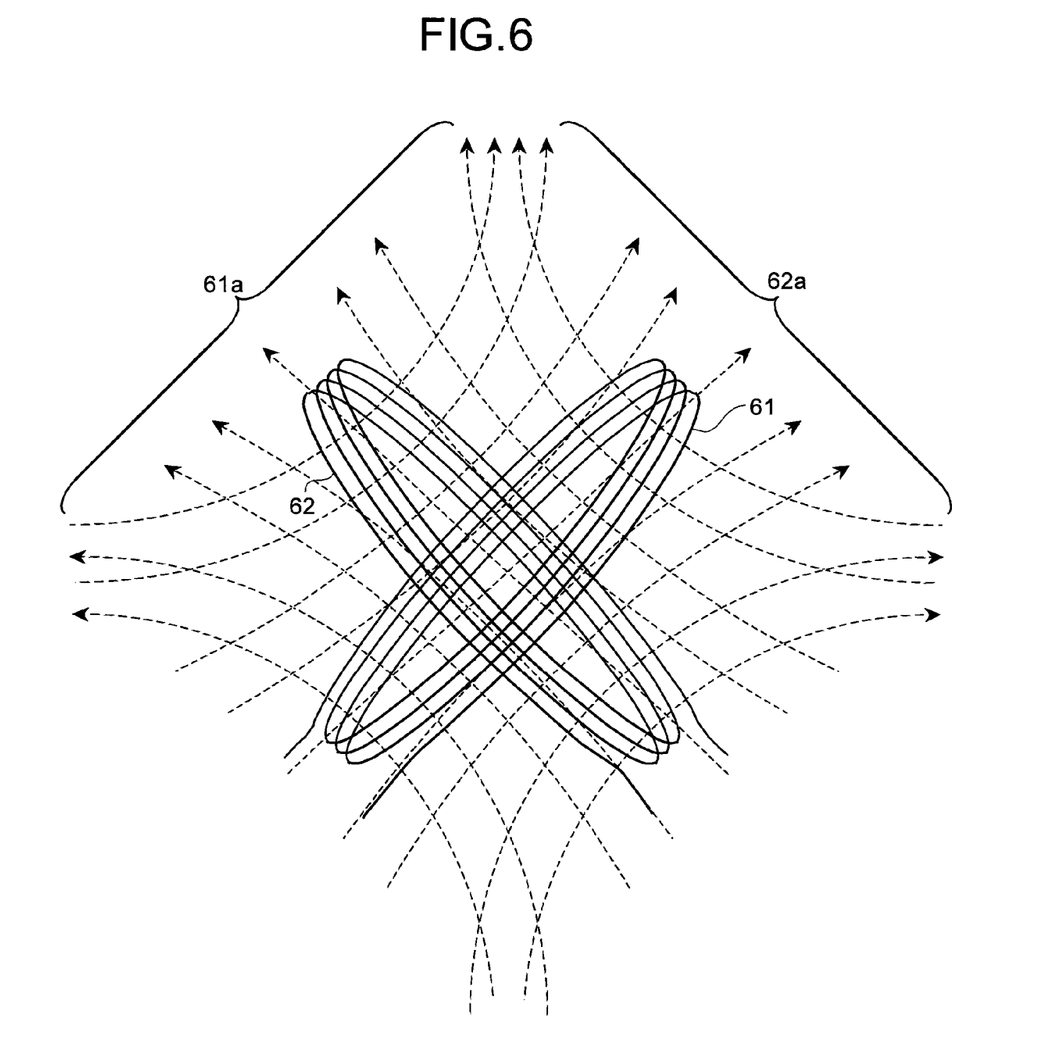
FIG. 6 shows a magnetic field generated by coils shown in FIG. 5.

The alternate current magnetic field generated by the coils 61 and 62 of FIG. 5 are shown in FIG. 6. In FIG. 6, the central axes of the coils 61 and 62 run orthogonally with each other. Magnetic fluxes 61a and 62a of the coils 61 and 62 radiate in plural directions and intersect with each other. Thus nondirectional alternate current magnetic field can be generated.

When the power supply unit 38 supplies power to the coils 61 and 62, electric current flows through the coils 61 and 62. Then, the plural magnetic fluxes 61a and 62a radiates in different direction so as to run through the coils 61 and 62, whereby the non-directional magnetic field is generated. When the capsule endoscope 2 introduced into the subject 1 reaches the magnetic field, induced electromotive force is generated in the power receiving coil 29a (see FIG. 3) due to the electromagnetic induction. Thus, the power is supplied to the inside of the capsule endoscope 2. In the figures following FIG. 6, only a magnetic field which is most relevant to the power supply is shown as a representative example.

Thus, in the first embodiment, two coils are arranged in the garment for power supply, run obliquely on the circumferential surface of the garment, and symmetrically arranged in a wound form, whereby the non-directional alternate current magnetic field is generated. Therefore, no matter how the orientation and the position of the capsule endoscope change in the subject within the alternate current magnetic field, the capsule endoscope still lies across the magnetic fluxes generated by the coil, whereby the generated induced electromotive force causes the power supply to the capsule endoscope. Thus, the capsule endoscope can efficiently receive power supply.

Additionally, since the generated alternate current magnetic field in the first embodiment is non-directional, only one coil is sufficient for the operation dissimilar to the conventional capsule endoscope which requires two or more coils with different directionalities for power reception. Thus, the first embodiment realizes stable power supply as well as space saving of the capsule endoscope.

The coils for power supply may additionally serve as the transmitting antenna shown in FIG. 4. In this case, the control signal input unit 36 of the external device 32 superposes various control signals on the power supply signal which is an alternate current signal supplied from the power supply unit 38. The control signal input unit 36 supplies the superposed signal to the capsule endoscope 2. Such configuration has the same advantages as those described above. In addition, such configuration allows elimination of the transmitting antennae in the external device, whereby the number of incorporated elements and manufacturing cost can be reduced. In the first embodiment, two electric cables are employed to form cross-arranged two coils. Two coils may be formed by one electric cable, however, when a manner of winding is changed.

Figure 7:
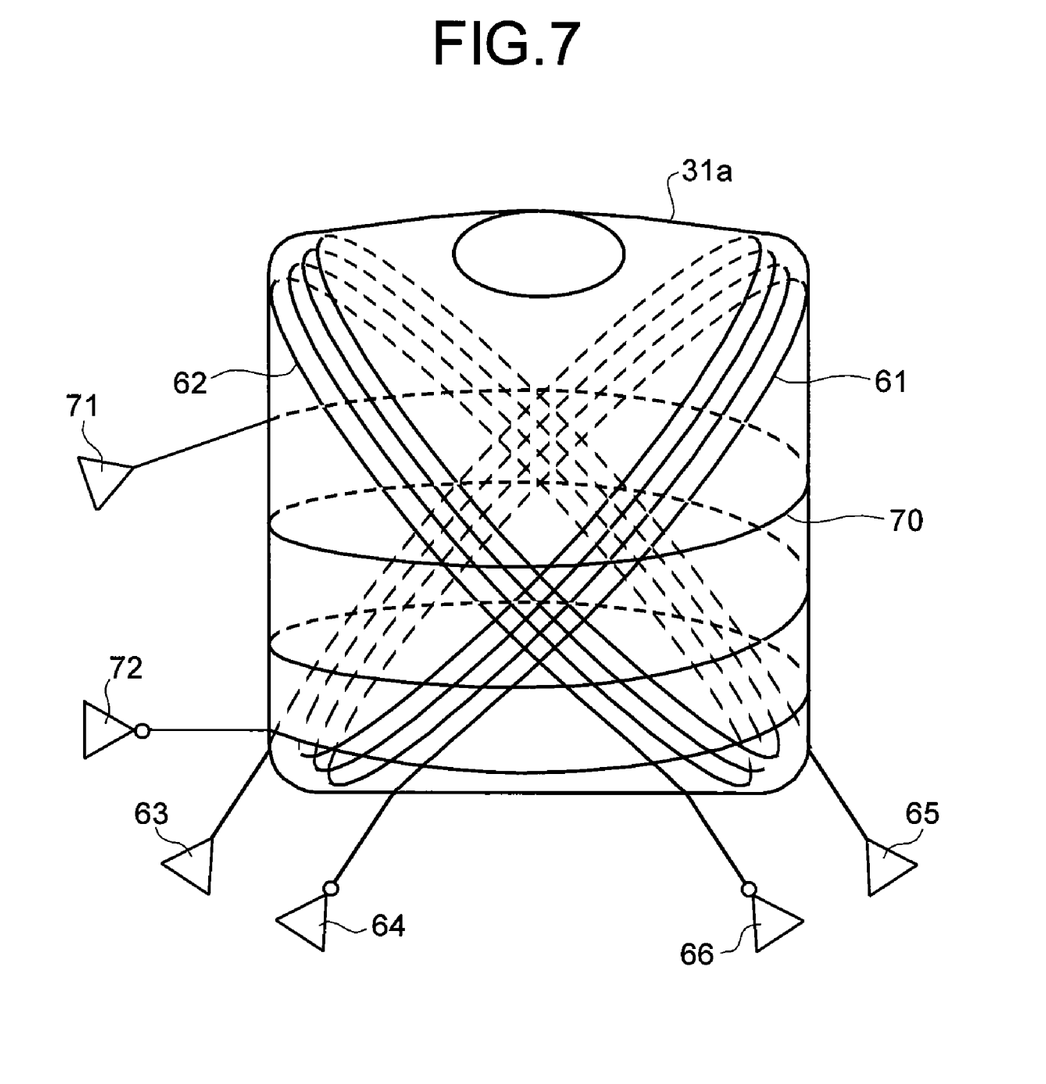
FIG. 7 is a frontal view showing a second embodiment of the vest shown in FIG. 1.

A second embodiment of the vest will be described with reference to FIG. 7. A vest 31a of FIG. 7 is different from the vest 31 of the first embodiment of FIG. 5 in that the vest 31a of FIG. 7 includes a coil 70 that runs along the inner circumferential surface of the vest in a horizontal direction. One electric cable is wound around a chest part of the vest and forms a spiral loop of a predetermined pitch as the coil 70. The coil 70 intersects with each of the coils 61 and 62 on a front side and a back side of the vest 31a.

The coil 70 is connected to driver circuits 71 and 72. The driver circuits 71 and 72 are further connected to the power supply unit 38 of the above-described external device 32. The power supply unit 38 supplies power. As a result of the power supply, an alternate current magnetic field of a predetermined strength is generated in the coil 70 similarly to the magnetic field generation in each of the coils 61 and 62.

Figure 8:
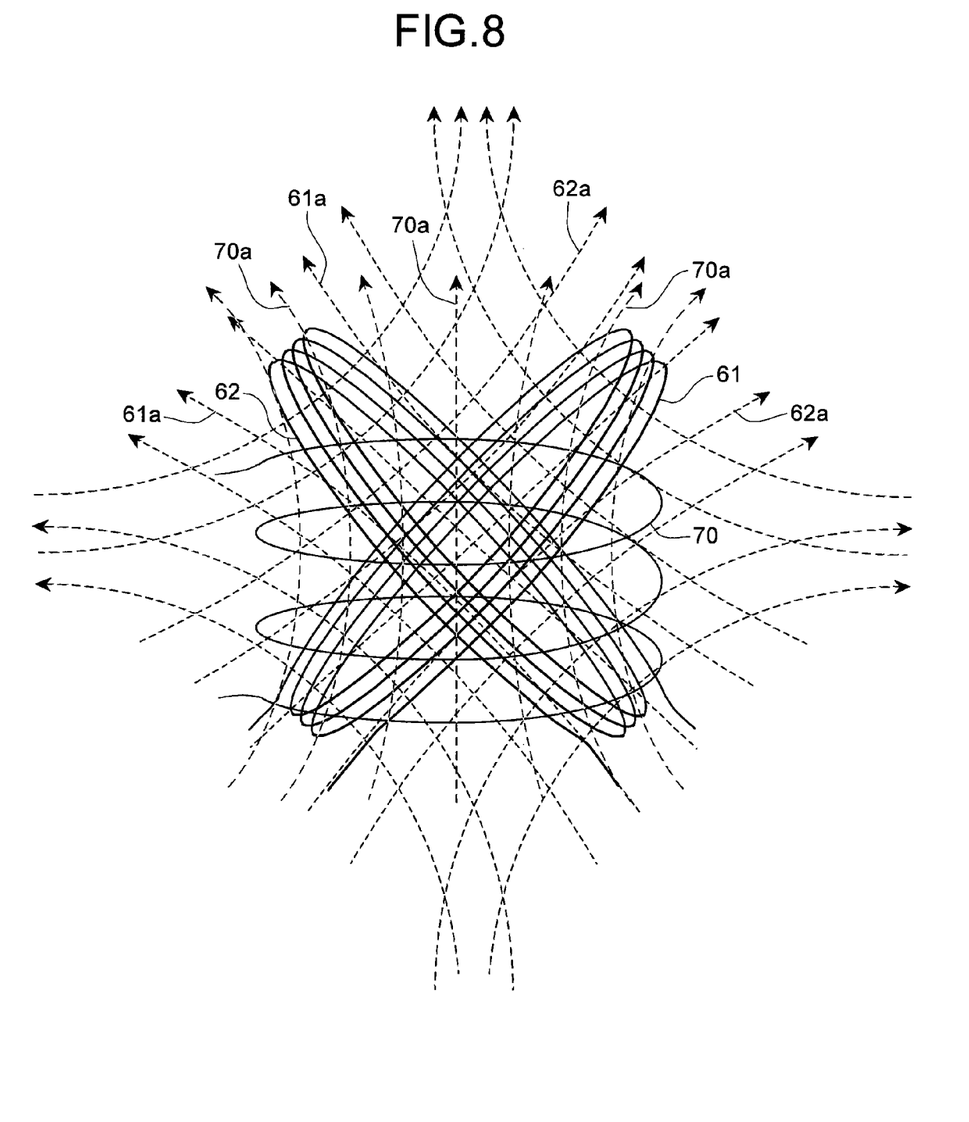
FIG. 8 shows a magnetic field generated by coils shown in FIG. 7.

Each of the coils 61, 62, and 70 of FIG. 7 generates an alternate current magnetic field as shown in FIG. 8. In FIG. 8, the magnetic fluxes 61a and 62a of the coils 61 and 62 are similar to those in the first embodiment. A magnetic flux 70a of the coil 70 radiates from a center, i.e., the horizontal central axis of the subject body and intersects with the magnetic fluxes 61a and 62a of the coils 61 and 62 with each other, whereby a non-directional alternate current magnetic field can be generated.

Similarly to the first embodiment, when the power supply unit 38 supplies power to the coils 61, 62, and 70, electric current flows through the coils 61, 62 and 70. Then, plural magnetic fluxes 61a, 62a, and 70a with different orientations are generated in directions intersecting with the coils 61, 62, and 70 to form a complicated magnetic flux arrangement, whereby a non-directional magnetic field is generated. When the capsule endoscope 2 in the subject 1 reaches the magnetic field, induced electromotive force is generated in the power receiving coil 29a(see FIG. 3) due to the electromagnetic induction. Thus the power is supplied to the inside of the capsule endoscope 2.

As described above, the garment 31a of the second embodiment is provided with two coils obliquely wound along the circumferential surface of the garment in a symmetrical manner, and one coil horizontally wound along the circumferential surface of the garment, for power supply. The generated alternate current magnetic field has more prominent non-directionality than the magnetic field of the first embodiment. Therefore, no matter how the orientation and the position of the capsule endoscope in the subject change, the capsule endoscope still intersects with the magnetic flux generated by the coils, whereby generated induced electromotive force causes power supply to the capsule endoscope. Thus, the capsule endoscope can receive power supply even more efficiently. In the second embodiment, similarly to the first embodiment, one electric cable may be sufficient to form three coils using a different manner of winding.

Figure 9:
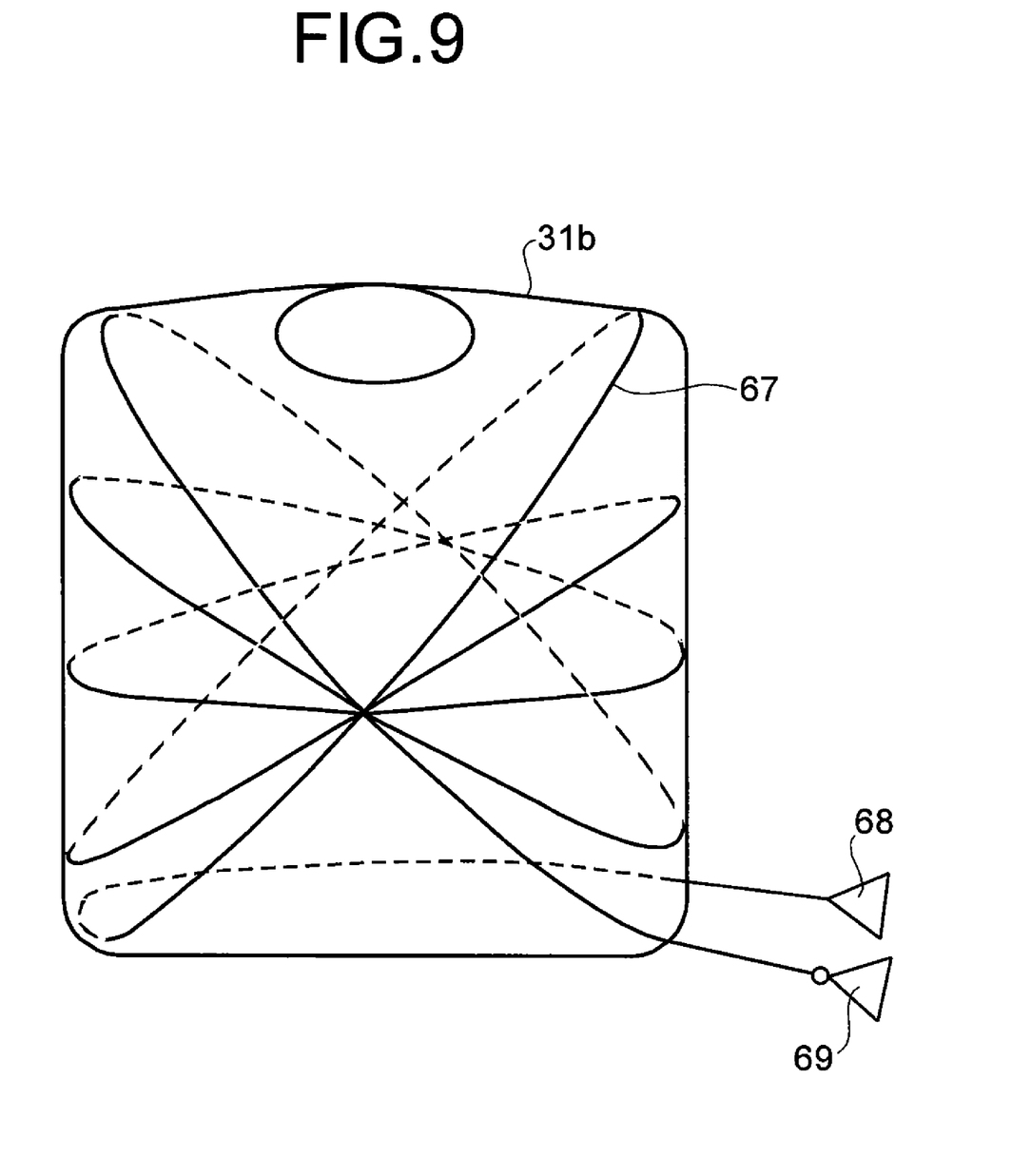
FIG. 9 is a frontal view showing a third embodiment of the vest shown in FIG. 1.

A third embodiment of the vest is described with reference to FIG. 9. In FIG. 9, a coil 67 is formed of one electric cable. The coil 67 runs around and is continuously wound around the vest 31b. The coil 67 forms an intersection at the front side and the back side of the vest and is placed at a predetermined horizontal pitch at both sides of the vest.

The coil 67 is connected to driver circuits 68 and 69. The driver circuits 68 and 69 are connected to the power supply unit 38 of the above-described external device 32. The power supply unit 38 supplies power. As a result of the power supply, an alternate current magnetic field of a predetermined strength is generated in the coil 67 similarly to the first and the second embodiments.

Specifically, central axes corresponding to respective loops of the coil 67 are arranged in a continuous manner, and the magnetic flux of the coil 67 radiates from the central axes. Then, the magnetic fluxes intersect with each other to further extend towards more various directions and further intersect with each other. Thus, the magnetic fluxes of the coil 67 come to have a complicated configuration, whereby a non-directional alternate current magnetic field can be generated in the third embodiment as well. In the third embodiment, when the power supply unit 38 supplies power to the coil 67, non-directional magnetic field is generated. When the capsule endoscope 2 in the subject 1 reaches the magnetic filed, induced electromotive force is generated in the power receiving coil 29a (see FIG. 3) due to electromagnetic induction, whereby the power is supplied to the inside of the capsule endoscope 2.

In the third embodiment, one coil is arranged in and continuously wound around the garment in such a manner that the coil intersects with itself at the front side and the back side of the garment on the circumferential surface thereof, and the portions of the coil are placed at a predetermined horizontal pitch at both sides of the garment. Therefore the resulting magnetic fluxes have more complicated manner of intersection compared with the magnetic fluxes of the first and the second embodiments, and the resulting alternate current magnetic field is non-directional. No matter how the orientation and the position of the capsule endoscope change in the subject, the capsule endoscope still intersects with the generated magnetic flux, whereby the generated induced electromotive force causes the power supply to the capsule endoscope. Thus, the capsule endoscope can receive power supply even more efficiently.

Figure 10:
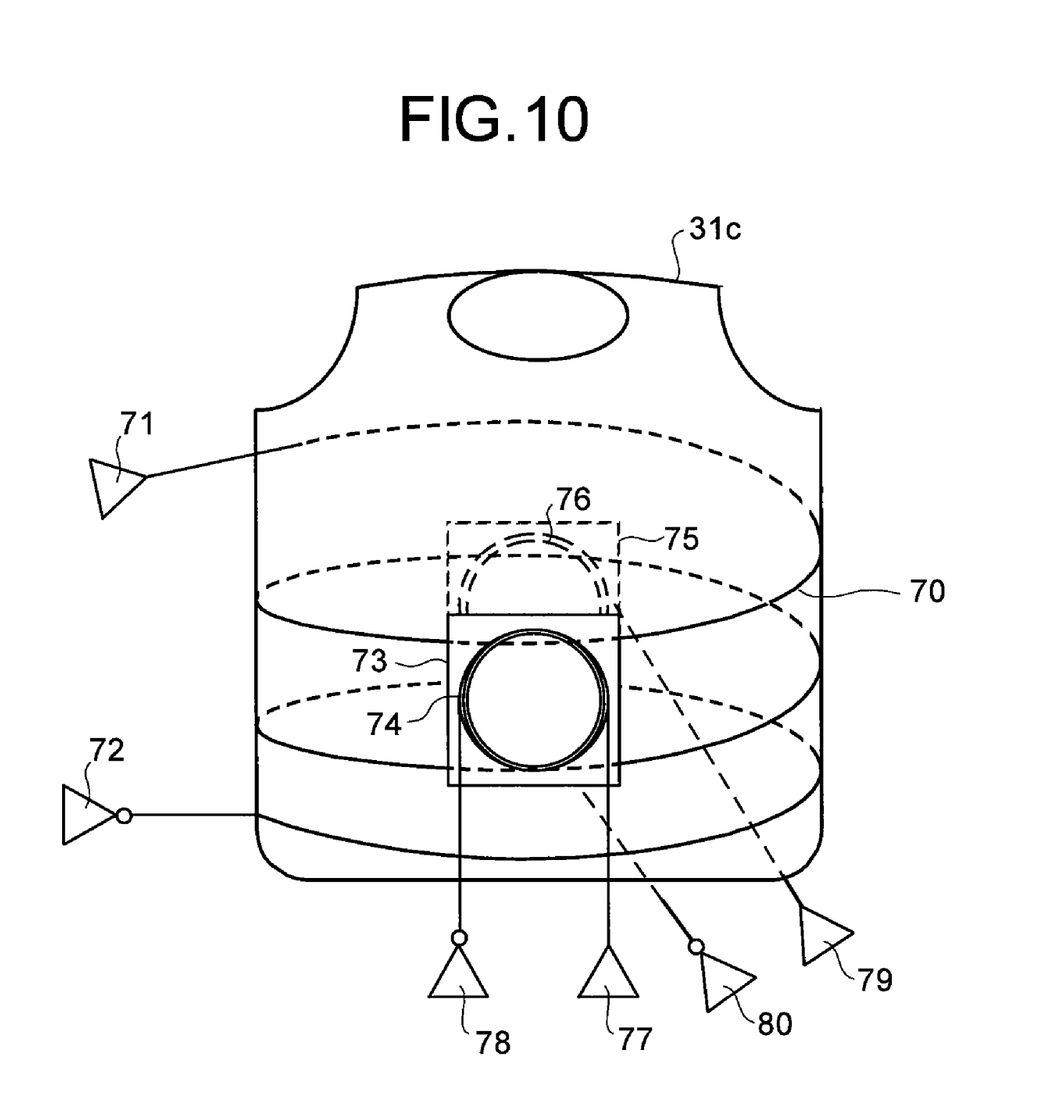
FIG. 10 is a frontal view showing a fourth embodiment of the vest shown in FIG. 1.

A fourth embodiment of the vest will be described with reference to FIG. 10. In FIG. 10, the vest 31c includes the coil 70 wound along the inner circumferential surface of the vest 31c and extends along the horizontal direction. The coil 70, similarly to the coil 70 in the second embodiment, is formed of one electric cable wound to form a spiral loop of a predetermined pitch. The coil 70 is connected to the power supply unit 38 of the external device 32 via the driver circuit 71 and 72. The power supply unit 38 supplies power. The magnetic fluxes 70a of the coil 70 radiate from a horizontal central axis of the subject body.

In the fourth embodiment, small sheet members 73 and 75 of a predetermined size are formed. An electric cable is wound and forms concentric spiral loops with the same diameter as a coil. Thus formed coils 74 and 76 are pasted onto the sheet members 73 and 75, respectively. The coil and the sheet member constitute a holding member which contributes to maintain the self-inductance of the coil at a stable level. One surface of each of the sheet members 73 and 75 has an adhesiveness to allow pasting of the coil. The sheet members 73 and 75 are pasted on the front side and the back side of the vest 31c, respectively, so that the sheet member 73 is placed opposite to the sheet member 75, and both sheet members 73 and 75 overlap with the coil 70. The coils 74 and 76 are connected to the power supply unit 38 of the external device 32 through the driver circuits 77 to 80. The power supply unit 38 supplies power. The sheet members 73 and 75 including the coils 74 and 76 can be pasted at any position as necessary.

Figure 11:
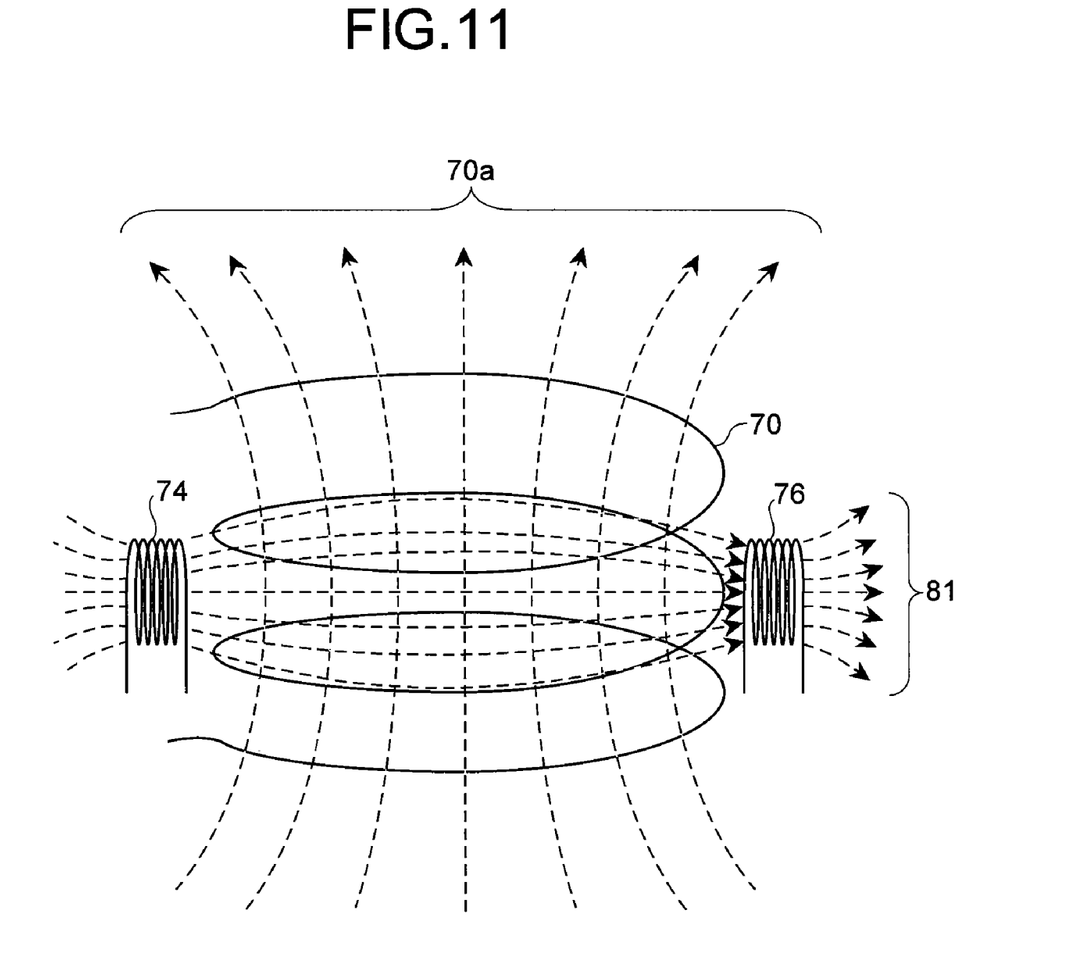
FIG. 11 shows a magnetic field generated by coils shown in FIG. 10.

The coils 70, 74, and 76 of FIG. 10 generate alternate current magnetic field as shown in FIG. 11. FIG. 11 shows the alternate current magnetic field seen from the side of the vest 31c. The magnetic flux 70a of the coil 70 shown in FIG. 8 radiates from the horizontal central axis of the subject body similarly to the magnetic flux of the second embodiment. The magnetic fluxes 81 of the coils 74 and 76 are converged around the central axis between the coils 74 and 76 so as to generate a uniform alternate current magnetic field. At the same time, the magnetic fluxes 81 intersect with the magnetic fluxes 70a of the coil 70. Thus, a non-directional alternate current magnetic field can be generated. Further, magnetic fluxes 81 extend outward (i.e., direction outside the subject) irradiating from the central axis.

When the power supply unit 38 supplies power to the coils 70, 74, and 76, electric current flows through the coils 70, 74, and 76, to generate the magnetic fluxes 70a and 81 with a different directionality so that the generated magnetic fluxes 70a and 81 pass through the coils 70, 74, and 76. When the capsule endoscope 2 reaches the magnetic field in the subject, induced electromotive force is generated in the power receiving coil 29a (see FIG. 3) due to the electromagnetic induction, whereby the power is supplied inside the capsule endoscope 2.

As described above, the garment of the fourth embodiment is provided with one coil horizontally wound around the circumferential surface of the garment and two patch-type coils together generating a magnetic field as a pair, for the power supply. Thus, the non-directional alternate current magnetic field is generated. Therefore, no matter how the orientation and the position of the capsule endoscope change in the subject, the capsule endoscope still intersects with the magnetic fluxes generated from the coils, whereby the power is supplied to the capsule endoscope due to the generated induced electromotive force. Thus, the capsule endoscope can receive the power supply even more efficiently. In addition, since the patch-type power supply coils are employed in the fourth embodiment, the alternate current magnetic field can be generated at any positions as necessary.

In the fourth embodiment, one set of the patch-type power supply coils are employed. The present invention is, however, not limited thereto. One patch-type power supply coil can also generate the same alternate current magnetic field as the magnetic field in the fourth embodiment. Needless to say, it is possible to employ plural pairs of patch-type power supply coils. The plural pairs may generate magnetic fluxes of plural different directionalities at the same position or at various positions, to form complicated intersections of magnetic fluxes. Then, the non-directionality of the generated alternate current magnetic field is further enhanced. The patch-type power supply coil of the fourth embodiment can be used in combination with the coils of the first to the third embodiments.

Figure 12:
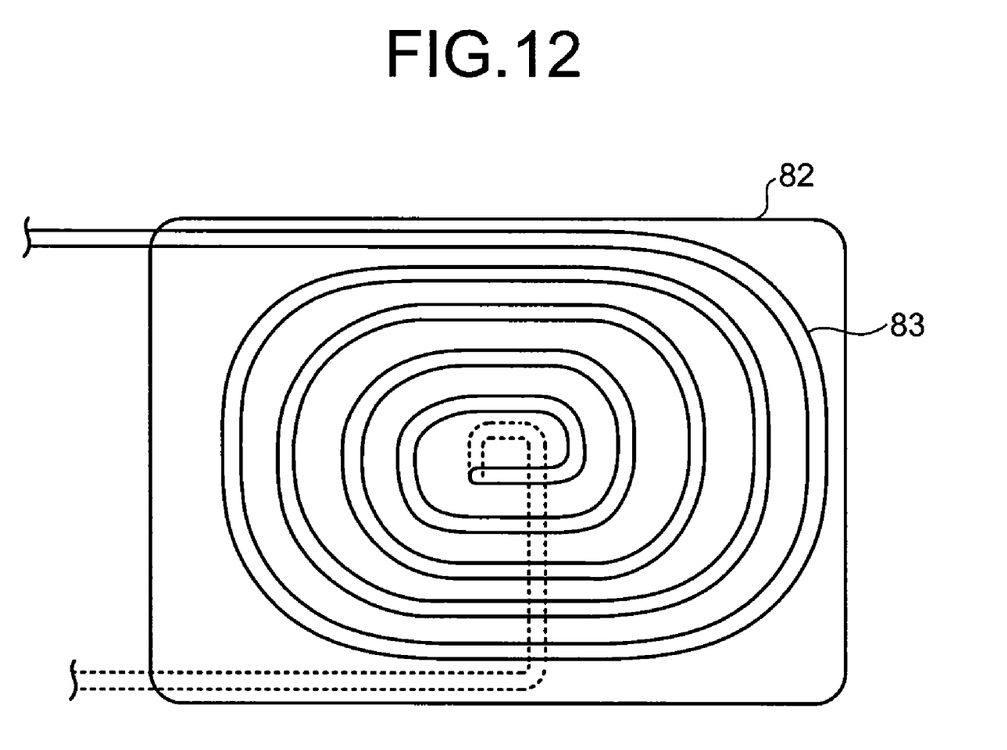
FIG. 12 shows another exemplary structure of a sheet member of FIG. 10 on which the coil is formed.

Another exemplary configuration of the sheet member including the coil as shown in FIG. 10 is shown in FIG. 12. In FIG. 12, a spirally-wound electric cable, i.e., a coil 83 is pasted onto a small sheet member 82 of a predetermined size, and forms a holding member. The holding member contributes to maintain the self-inductance of the coil at a stable level. When the power supply unit 38 supplies power to the coil 83 through driver circuits (not shown), electric current flows through the coil 83 to generate similar magnetic fluxes as those of the coils 74 and 76 shown in FIG. 11. One surface of the sheet member 82 has adhesiveness to allow pasting of the coil.

When the sheet member 82 with the above-described configuration is pasted onto the garment provided with the coil 70; or when at least one sheet member 82 is pasted onto the subject body; or when at least two sheet members 82 are pasted onto the front side and the back side, respectively, of the garment or the subject body; or when at least two sheet members 82 are pasted onto the right and the left sides, respectively, of the garment or the subject body, a non-directional alternate current magnetic field can be generated. These configurations achieve the same advantages as those of the fourth embodiment. The coil in the sheet member of FIG. 12 is formed to have concentric loops of different diameter and hence the loops do not need to overlap with each other as in the sheet member of FIG. 10. Therefore, the sheet member of FIG. 12 can be made thinner than the sheet member of FIG. 10.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A power supply apparatus which supplies power to a body-insertable apparatus from outside a subject, the body-insertable apparatus being introduced into the subject and obtaining intra-subject information, the power supply apparatus comprising:
   a garment that covers the subject;
   a power-supply coil having loops with non-concentric central axes and arranged in and continuously wound around the garment to intersect with itself at a front side and a back side of the garment on an inner circumferential surface of the garment, the power-supply coil being placed at a predetermined horizontal pitch at both sides of the garment; and
   a power supply unit that supplies power to the body-insertable apparatus in a contactless manner through the power-supply coil.

* * * * *